United States Patent
Herrmann (10) Patent No.: US 12,367,598 B2
(45) Date of Patent: Jul. 22, 2025

(54) TECHNIQUE OF GENERATING SURGICAL INFORMATION FROM INTRA-OPERATIVELY AND PRE-OPERATIVELY ACQUIRED IMAGE DATA

(71) Applicant: Stryker European Operations Limited, Carrigtwohill (IE)

(72) Inventor: Florian Herrmann, Schwanau (DE)

(73) Assignee: Stryker European Operations Limited, Carrigtwohill (IE)

( * ) Notice: Subject to any disclaimer, the term of this patent is extended or adjusted under 35 U.S.C. 154(b) by 373 days.

(21) Appl. No.: 17/837,351

(22) Filed: Jun. 10, 2022

(65) Prior Publication Data

US 2022/0398755 A1     Dec. 15, 2022

(30) Foreign Application Priority Data

Jun. 15, 2021   (EP) .................................. 21179565

(51) Int. Cl.
  *G06T 7/00*   (2017.01)
  *A61B 90/00*  (2016.01)
  (Continued)

(52) U.S. Cl.
  CPC ............ *G06T 7/337* (2017.01); *A61B 90/361* (2016.02); *G16H 30/40* (2018.01); *G06T 2207/20221* (2013.01); *G06T 2207/30012* (2013.01)

(58) Field of Classification Search
  CPC .......... G06T 7/337; G06T 2207/20221; G06T 2207/30012; A61B 90/361; G16H 30/40
  See application file for complete search history.

(56) References Cited

U.S. PATENT DOCUMENTS 9,265,463 B1 *   2/2016   Hipp ..................... A61B 6/468
10,368,956 B2    8/2019   Siewerdsen et al.
(Continued)

FOREIGN PATENT DOCUMENTS

EP    3184071 A1    6/2017
EP    3375399 A2    9/2018
(Continued)

OTHER PUBLICATIONS

English language abstract for EP 3 184 071 A1 extracted from espacenet.com database on Jun. 13, 2022, 2 pages.

*Primary Examiner* — Khai M Nguyen
(74) *Attorney, Agent, or Firm* — Howard & Howard Attorneys PLLC (57) ABSTRACT

A technique of generating surgical information from intra-operatively acquired image data of vertebrae and pre-operatively acquired image data of the vertebrae is presented. A method implementation includes obtaining first image segments each containing a different vertebra, and second image segments each containing a different vertebra. The first image segments have been derived by processing the pre-operatively acquired image data, and the second image segments have been derived by processing the inter-operatively acquired image data. The method includes identifying one of the second image segments and one of the first image segments that contain the same vertebra, and determining a transformation that registers the identified first image segment and the identified second image segment. The method includes generating surgical information based on the transformation and the identified first image segment.

18 Claims, 6 Drawing Sheets

(51) Int. Cl.
*G06T 7/33* (2017.01)
*G16H 30/40* (2018.01)

(56) References Cited

U.S. PATENT DOCUMENTS

| | | | |
|---|---|---|---|
| 10,524,865 | B2 | 1/2020 | Trousset et al. |
| 10,743,943 | B2 | 8/2020 | Razeto et al. |
| 11,911,110 | B2* | 2/2024 | Snyder .................... G06T 7/246 |
| 2003/0086596 | A1* | 5/2003 | Hipp .................... G06T 7/0012 |
| | | | 382/128 |
| 2017/0135661 | A1* | 5/2017 | Hipp .................... A61B 6/5235 |
| 2017/0231713 | A1 | 8/2017 | Siewerdsen et al. |
| 2018/0092699 | A1* | 4/2018 | Finley .................... A61B 34/20 |
| 2018/0368921 | A1 | 12/2018 | Jeszenszky et al. |
| 2020/0311864 | A1 | 10/2020 | Hamauzu |
| 2020/0327721 | A1 | 10/2020 | Siemionow et al. |
| 2022/0061919 | A1* | 3/2022 | Destainville ........... A61B 34/10 |
| 2024/0315778 | A1* | 9/2024 | Sarvestani ............. A61B 90/37 |

FOREIGN PATENT DOCUMENTS

| | | |
|---|---|---|
| EP | 3714792 A1 | 9/2020 |
| WO | 9611624 A2 | 4/1996 |
| WO | 2011134083 A1 | 11/2011 |
| WO | 2020129034 A1 | 6/2020 |

* cited by examiner

Fig. 3B
(pre-operative image data)

Fig. 3A
(intra-operative image data)

TECHNIQUE OF GENERATING SURGICAL INFORMATION FROM INTRA-OPERATIVELY AND PRE-OPERATIVELY ACQUIRED IMAGE DATA

PRIORITY CLAIM

This application claims priority under 35 U.S.C. § 119 to European Patent Application No. 21179565.3, filed Jun. 15, 2021, the entire contents of which are hereby incorporated by reference.

TECHNICAL FIELD

The present disclosure generally relates to the provision of surgical assistance. In more detail, a technique of generating surgical information from intra-operatively and pre-operatively acquired image data of vertebrae is provided. The technique may be implemented as a method, a computer-program product or an apparatus.

BACKGROUND

Spinal interventions have become a widespread surgical treatment and are currently performed either manually by a surgeon or by a surgical robot.

To guarantee proper surgical results, surgical information may be exploited to pre-operatively plan a spinal intervention or to intra-operatively navigate a tracked surgical tool relative to a particular vertebra, or for other purposes. The surgeon or surgical robot may for example be guided or controlled, based on the surgical information, to advance the surgical tool along a pre-planned trajectory towards the vertebra.

The surgical information is often generated based on image data acquired using a radiation-based imaging technology such as computer tomography (CT). To reduce the radiation exposure for a patient and surgical personnel, especially intra-operative image data are often acquired using low-dose imaging techniques such as cone beam CT (CBCT) or using two-dimensional CT scout images. The drawback of such low-dose imaging techniques is the low resolution of the resulting image data, which also impairs the precision of any surgical information derived therefrom. While alternative imaging techniques such as ultrasound imaging do exist, such alternative imaging techniques inherently have a low resolution and, thus, suffer from similar drawbacks when it comes to the generation of surgical information.

WO 2011/134083 A1 relates to a technique for generating intra-operative guidance feedback. Pre-operatively acquired three-dimensional image data associated with a patient is registered to intra-operatively acquired topological data obtained by a surface topology imaging device that evaluates backscattered radiation. The pre-operatively acquired image data for a given orthopedic structure is segmented into structure segments that have rotational and translational degrees of freedom with respect to one another (e.g., individual vertebrae). Each of the image data segments can then be registered to the back-scattered radiation topology scan using surface registration.

U.S. Pat. No. 10,368,956 B2 teaches a technique for segmenting structures of interest in pre-operatively acquired three-dimensional image data and generating a simulated projection of the segmented structures to be aligned, or registered, with an inter-operatively acquired two-dimensional projection image of the structures of interest. In this manner, the typically superior image quality and better three-dimensional anatomic context of the pre-operatively acquired three-dimensional image data can be added to the information obtained from the two-dimensional projection image to assist the surgeon.

It has been found that the information enhancement associated with a technique of the type presented in U.S. Pat. No. 10,368,956 B2, or other types, is often not sufficient for certain navigation purposes, in particular in the context of a spinal intervention.

SUMMARY

There is a need for a technique of generating surgical information from intra-operatively acquired image data of vertebrae and pre-operatively acquired image data of the vertebrae that yields an improvement in regard to the surgical information.

According to a first aspect, a method of generating surgical information from intra-operatively acquired image data of vertebrae and pre-operatively acquired image data of the vertebrae is provided. The method comprises obtaining first image segments each containing a different vertebra, wherein the first image segments have been derived by processing the pre-operatively acquired image data, and obtaining second image segments each containing a different vertebra, wherein the second image segments have been derived by processing the inter-operatively acquired image data. The method also comprises identifying one of the second image segments and one of the first image segments that contain the same vertebra, and determining a transformation that registers the identified first image segment and the identified second image segment. Further still, the method comprises generating surgical information based on the transformation and the identified first image segment.

The surgical information may be output to a surgical robot (e.g., as a data set that, optionally, has been processed further for this purpose). Alternatively, or in addition, the surgical information may be output to a surgeon (e.g., acoustically via a loudspeaker or visualized on a display device). The surgical information may be used for one or both of surgical planning and surgical navigation.

The intra-operatively acquired image data may reflect a current position and orientation of at least one of the vertebrae in which the at least one vertebra will be subjected to a surgical intervention. The term "intra-operatively" may also encompass a point in time at which the patient is already placed on an operating table, while the spinal intervention as such (including, e.g., an incision to provide a vertebral access through the patient's skin) has not yet started.

The pre-operatively acquired image data may be of the same spatial dimension as the intra-operatively acquired image data. For example, both types of image data may be three-dimensional image data. In some variants, the pre-operatively acquired image data are three-dimensional image data and the intra-operatively acquired image data are two-dimensional image data.

Generating the surgical information may comprise processing the intra-operatively acquired image data based on the identified first image segment and the transformation. The intra-operatively acquired image data may for example be processed in a spatial region of the identified second image segment. In some variants, the spatial region of the identified second image segment may be defined by the transformation (e.g., in the form of a translational transformation component). In such or other variants, the transformation may (e.g., additionally) define a rotation (e.g., in the form of a rotational transformation component).

Processing of the intra-operatively acquired image data may comprise blending the identified first image segment into the intra-operatively acquired image data with the transformation being applied to the first image segment. As such, the intra-operatively acquired image data may locally (e.g., in a spatial region of the identified second image segment) be modified using the first image segment. The modification may in some variants result in a locally enhanced image data resolution so as to improve accuracy of the surgical information (e.g., compared to a scenario in which the surgical information is generated solely based on the intra-operatively acquired image data).

The steps of identifying, determining and generating may individually be performed for two or more of the first image segments and two or more of the second image segments, respectively. As an example, multiple first image segments relating to different vertebrae may be blended into the intra-operatively acquired image data at their proper position and orientation as defined by the respectively associated second image segment and the respectively associated transformation.

Processing of at least one of the pre-operatively and the intra-operatively acquired image data may comprise segmenting the respective image data into separate regions associated with individual vertebrae. Processing of at least one of the pre-operatively and the intra-operatively acquired image data may comprise determining boundaries in the respective image data between pairs of adjacent vertebrae. In case the image data are of dimension N, the boundaries may be of dimension N−1. In the exemplary case of three-dimensional image data, the boundaries may thus be defined by two-dimensional geometric objects (e.g., a flat plane or a warped plane that depends on the surface contour of a given vertebra in its region facing towards an adjacent vertebra). In the case of two-dimensional image data, the boundaries may be defined by one-dimensional geometric objects (e.g., a straight line or a bent line that depends on the surface contour of a given vertebra in its region facing towards an adjacent vertebra).

Processing of at least one of the pre-operatively and the intra-operatively acquired image data may comprise determining, for an individual vertebra, a bounding volume containing the individual vertebra. The bounding volume for the individual vertebra may in some variants be limited by the boundaries towards its adjacent vertebrae (e.g., flat or warped planes) and a lateral enclosure (e.g., a closed circumferential wall) extending between the two boundaries. In case the image data are of dimension N, the bounding volume may also be of dimension N.

Processing of at least one of the pre-operatively and the intra-operatively acquired image data may comprise performing surface identification to identify a vertebra surface for each individual vertebra. The vertebra surface may be defined in one dimension (e.g., as a closed line) or two dimensions (e.g., as a mesh and/or a closed hollow body). The surface identification for an individual vertebra may be performed in a subset of the respective image data defined by the bounding volume containing the individual vertebra.

At least one of the first image segments and the second image segments may be defined by, consist of or comprise the vertebra surface of the vertebra contained therein. The image segments may be of the same dimension as the underlying image data or of a lower dimension.

The method may also comprise identifying, in at least one of the pre-operatively and the intra-operatively acquired image data, at least one vertebral landmark for each individual vertebra. Exemplary vertebral landmarks comprise dedicated points of one or both of the spinous process and the superior articular facet.

The transformation may be determined by matching (e.g., registering) at least one of the vertebra surfaces and the vertebra landmarks (depending on their availability) in the identified second image segment and the identified first image segment. The transformation may comprise at least one of a translational transformation component and a rotational transformation component. The respective translational component may correlate a center of gravity in the (optionally further processed) identified first image segment (e.g., the respective vertebra surface or bounding volume) with a center of gravity of the (optionally further processed) identified second image segment (e.g., the respective vertebra surface or bounding volume).

If, for example, the image segments are provided in the form of surface information (e.g., as surface meshes) of the individual vertebrae, the center of gravity may be determined first for each image segment. Then, the centers of gravity of the identified second image segment and the identified first image segment may be matched (e.g., by a translation), followed by an alignment of the respective landmarks (e.g., by a rotation and/or a further translation). In an optional further step, a surface matching is performed to "fine tune" the transformation parameters.

In some variants, landmark alignment may be omitted, and the matching of the centers of gravity may directly be followed by surface matching. In still further variants, only surface matching is performed.

The first image segments (e.g., the respective vertebra surface or bounding volume) and the second image segments (e.g., the respective vertebra surface or bounding volume) may each be associated with an individual coordinate system. The transformation may register the coordinate system of the identified second image segment and the coordinate system of the identified first image segment.

The method may comprise determining at least one of a rotation and a translation of an individually tracked vertebra during a spinal intervention. This determination may be made in real-time using a surgical tracking system comprising one or more trackers coupled to one or more vertebrae. The determination may be made in 5 or 6 degrees of freedom (DOF). The method may further comprise taking into account the at least one of the rotation and the translation when generating the surgical information. As an example, when the surgical information is visually output to the surgeon during the spinal intervention, any rotation or translation of the tracked vertebra relative to a coordinate system of the surgical tracking system may be visualized also, in particular in real-time.

The method may comprise obtaining labelling information that labels at least some of the first and second image segments (e.g., by a type of vertebra contained therein). The labelling information may be a conventional notation as known in the art (i.e., L1 to L5, etc.) or a proprietary notation. The labelling information may be input by a user (e.g., the surgeon or other medical personnel), or it may be determined automatically.

Identifying the first and second image segment that contain the same vertebra may be performed based on the labelling information. For example, the first and second image segment associated with the same label may be determined to contain the same vertebra. Labels may be attributed to the first and second image segments by matching each image segment (i.e., information contained therein)

with generic vertebra models each defining a dedicated label. Surface matching may be used in case the generic vertebra models are provided in the form of surface models. In addition, or as an alternative, the labels may be attributed by exploiting an anatomic context of each of the first and second image segment (e.g., in regard to adjacent anatomic structures).

The intra-operatively acquired image data may be indicative of at least one of the relative positions and the relative orientations between the vertebrae during a spinal intervention. At least one of the pre-operatively acquired image data and the intra-operatively acquired image data (and especially both types of image data) may be representative of a three-dimensional image volume (e.g., in the DICOM format). At least one of the pre-operatively acquired image data and the intra-operatively acquired image data may have been generated using a medical imaging technique, such as CT, ultrasound imaging and magnetic resonance imaging (MRI), in particular magnet resonance tomography (MRT). The medical imaging technique may in particular be a projection-based technique that exploits radiation such as X-rays (e.g., CT).

The pre-operatively acquired image data may have a higher resolution than the intra-operatively acquired image data. For example, the pre-operatively acquired image data may be CT data of inherently higher resolution, and the intra-operatively acquired image data may acquired using ultrasound, CBCT, intra-operative CT or two-dimensional CT scout image data of lower resolution.

Also provided is a computer program product comprising program code portions that cause a processor to perform the method presented herein when the computer program product executed by the processor. The computer program product may be stored on a CD-ROM, semiconductor memory, or it may be provided as a data signal.

Further, an apparatus is provided for generating surgical information from intra-operatively acquired image data of vertebrae and pre-operatively acquired image data of the vertebrae. The apparatus is configured to obtain first image segments each containing a different vertebra, wherein the first image segments have been derived by processing the pre-operatively acquired image data, and to obtain second image segments each containing a different vertebra, wherein the second image segments have been derived by processing the inter-operatively acquired image data. The apparatus is also configured to identify one of the second image segments and one of the first image segments that contain the same vertebra, and to determine a transformation that registers the identified first image segment and the identified second image segment. Moreover, the apparatus is configured to generate surgical information based on the transformation and the identified first image segment.

In some variants the apparatus is configured to obtain at least one of the first and second image segments via a data carrier, a data link or a data interface, wherein the underlying processing (e.g., segmenting that yields the first and second image segments) of the pre-operatively and intra-operatively acquired image data has been performed by a different entity. In other variants the apparatus is also configured to process at least one of the pre-operatively and intra-operatively acquired image to obtain at least one of the first and segment image segments.

The apparatus may further be configured to perform any aspect of the method presented herein.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following description of exemplary embodiments of the present disclosure, the same reference numerals are used to denote the same or similar components.

While the following embodiments will primarily be described in the context of generating visual navigation information to assist a surgeon guide a surgical tool during a spinal intervention, it will be appreciated that the navigation information could alternatively, or additionally, be used to control a surgical robot that operates in a fully automated or semi-automatic manner. As understood herein, a semi-automatic operation includes a scenario in which the handling of a surgical tool by a surgeon is constrained by the surgical robot. Further, the surgical information could be used for surgical planning purposes.

Figure 1A:
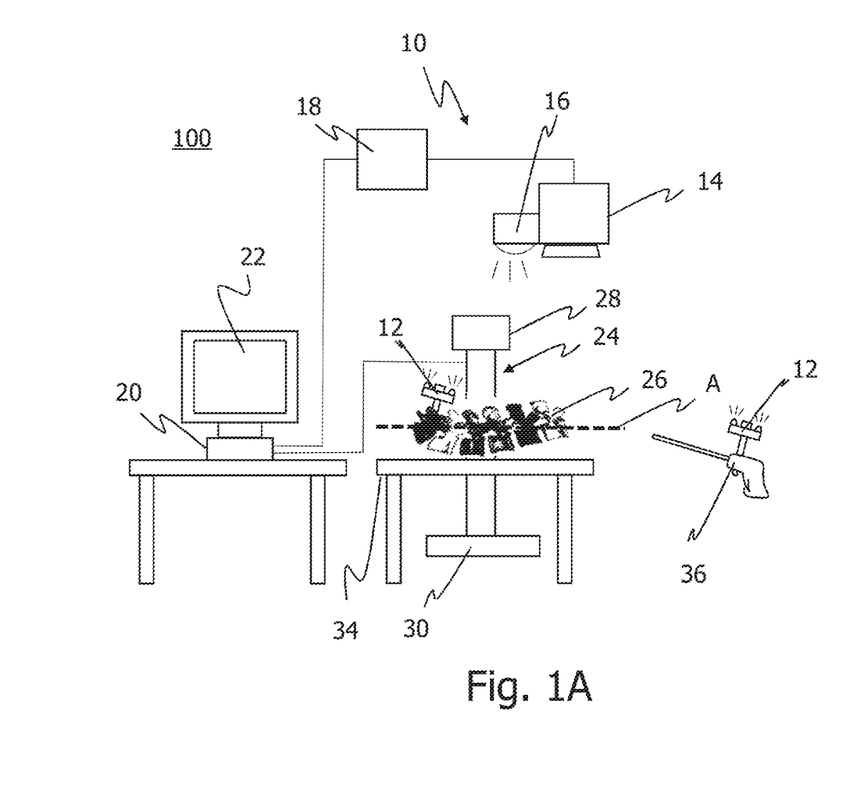
FIG. 1A schematically illustrates a surgical system comprising an apparatus for generating surgical information according the present disclosure.

FIG. 1A schematically illustrates an embodiment of a surgical system 100 installed at a surgical site (e.g., in an operating room). The surgical system 100 comprises a surgical tracking system 10 including one or more trackers 12, a camera 14, an optional source of electromagnetic radiation 16, and a tracking controller 18.

The surgical system 100 further comprises an apparatus 20 that is configured to generate surgical information and an output device 22 that is configured to output the surgical information to a surgeon. In the present scenario, the output device 22 is a display device configured to visually output the surgical information to the surgeon. In other variants, the output device may be configured to (e.g., additionally or alternatively) output one or more of acoustic and haptic surgical information. As such, the output device could also be configured as an augmented reality device (e.g., as a head-mounted display, HMD), as a loudspeaker, as an actuator configured to generate haptically detectable surgical information, or as a combination thereof.

In FIG. 1A, the apparatus 20 is realized as a local computer system situated in the operating room. Alternatively, the apparatus 20 may be realized in the form of a remote server or in the form of cloud computing resources. The apparatus 20 and the tracking controller 18 are illustrated as two separate entities. Alternatively, the apparatus 20 and the tracking controller 18 may jointly be provided as, or be part of, a single apparatus or by cloud computing resources.

The surgical system 100 of FIG. 1A further comprises an imaging apparatus 24 that is configured to intra-operatively acquire image data of a patient's vertebrae 26. In the exemplary scenario illustrated in FIG. 1A, the imaging apparatus 24 is configured to generate projection images. In more detail, the imaging apparatus is a C-arm with CBCT imaging capabilities. The imaging apparatus 24 comprises a radiation source 28 configured to generate a cone-shaped beam of radiation. Moreover, the imaging apparatus 24 has a flat-panel detector 30 configured to detect the radiation beam projected by the radiation source 28 through the vertebrae 26. The detector 30 is configured to generate image data representative of a two-dimensional projection image of the vertebrae 26 per imaging step.

Figure 1B:
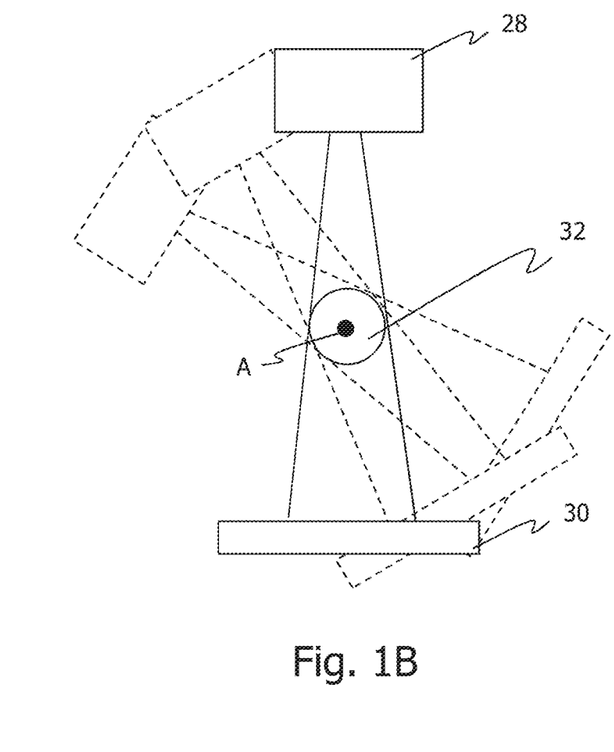
FIG. 1B illustrates a schematic view of an imaging apparatus configured to intra-operatively generate image data according to the present disclosure.

As illustrated in FIG. 1B, such projection images of an imaged volume 32 containing the vertebrae 26 are taken at two more angular orientations of the C-arm relative to an imaginary longitudinal axis A of the vertebrae 26. From the resulting two-dimensional projection images, a three-dimensional image volume of the vertebrae 26 may in some variants be intra-operatively acquired by reconstruction (e.g., back-projection) techniques. The reconstruction may be performed either by the imaging apparatus 24 or by the apparatus 20 that generates the surgical information.

The intra-operatively acquired image data are indicative of the current relative positions and orientations of the vertebrae 26 during the spinal intervention (e.g., with the patient being placed on an operating table 34, see FIG. 1). The intra-operatively acquired image data thus help to improve the precision of real-time navigation.

In the scenario discussed here, the apparatus 20 will generate the surgical information based on intra-operatively acquired three-dimensional image data. It will be appreciated that in other scenarios, the surgical information may be generated based on intra-operatively acquired two-dimensional image data, such as a single CBCT projection image or two (or more) two CBCT projection images.

Turning now to the tracking system 10 in FIG. 1A, the source of electromagnetic radiation 16 is configured to emit at least one of infrared light and visible light. The source of electromagnetic radiation 16 may specifically be configured to flood the entire surgical site with electromagnetic radiation. Each of the one or more trackers 12 comprises three or more reflectors (e.g., spherically shaped bodies) that reflect the electromagnetic radiation emitted by the source of electromagnetic radiation 16. As such, the one or more trackers 12 are configured as so-called passive trackers. In other variants, at least one of the one or more trackers 12 may be realized as an active device configured to emit electromagnetic radiation. As an example, each active tracker 12 may comprise three or more light emitting diodes (LEDs) emitting electromagnetic radiation in the infrared or visible spectrum. If all the trackers 12 are configured as active devices, the source of electromagnetic radiation 16 may in some variants be omitted.

The camera 14 of the tracking system 10 has at least one image sensor, such as a charged couple device (CCD) or a complementary metal-oxide-semiconductor sensor (CMOS). The image sensor is configured to detect the electromagnetic radiation reflected (or emitted) by the one or more trackers 12. In some variants, the camera 14 may have multiple image sensors 24. In particular, the camera 14 may be a stereo camera with at least two image sensors 24.

The tracking controller 18 is configured to process the image data generated by the at least one image sensor 24 and to calculate the position and orientation of the one or more trackers 12 in a tracking coordinate system. This calculation is typically performed in 5 or 6 DOF. The tracking coordinate system may have a rigid relationship relative to the camera 14 and may in particular be centred in a centre of the camera 14.

In the exemplary scenario illustrated in FIG. 1A, a dedicated tracker 12 is provided for a surgical tool 36 (e.g., a surgical pointer, drill or screwdriver) and at least one of the vertebrae 26. In case the spinal intervention is to take place at multiple ones of the vertebrae 26, each of those multiple vertebrae 26 may be tracked individually. While not illustrated in FIG. 1A, a further tracker 12 may be associated with the imaging apparatus 24 to allow for an easy initial registration between an imaging coordinate system in which the intra-operatively acquired image data are obtained by the imaging apparatus 24 and the tracking coordinate system associated with the camera 14. Of course, the registration could also be performed using other techniques, such as the surgeon pointing at dedicated vertebral landmarks using a tracked surgical pointer.

As shown in FIG. 1A, the apparatus 20 for generating surgical information is communicatively coupled with the tracking controller 18, the imaging apparatus 24 and the output device 22. In some variants of the present disclosure, the apparatus 20 performs the initial registration step described above. In those or other variants, the apparatus 20 is configured to generate surgical information based on the data inputs from the tracking controller 18 (e.g., the position and orientation of the tracked surgical tool 36 in the tracking coordinate system) and the (registered) two-dimensional or three-dimensional image data intra-operatively acquired by the imaging apparatus 24. Such surgical information can be navigation information representative of a current trajectory or a current tip position of the tracked surgical tool 36 relative to one or more of the imaged vertebrae 26. The navigation information thus generated may then be output via the output device 22 to the surgeon. In case the surgeon is replaced or assisted by a surgical robot, the navigation information is output as a data set to the surgical robot for control or verification purposes. The surgical information can also be planning information (e.g., for planning an implant type or size, for trajectory planning, for tumor segmenting, etc.)

If the vertebrae 26 are tracked also (either individually or collectively), any movement of the one or more tracked vertebrae 26 will be detected by the tracking system 10 (in 5 or 6 DOF). The movement, which can involve one or both of a rotation and a translation, can then be considered by the apparatus 20 in real-time upon generating the surgical information by, for example, updating a visual representation of the vertebrae 26.

Surgical information generated based on CBCT or similar intra-operatively usable imaging techniques (e.g., ultrasound imaging or using two-dimensional CT scout images) are particularly helpful as they consider the intra-operative relative positions and orientations of the imaged vertebrae 26 and their intra-operative anatomical context. Also, such intra-operative imaging techniques often involve low radiation doses. On the other hand, the precision of intra-operatively acquired image data is often less-than-optimal, for example in regard of one or both of the precise anatomical context and image resolution.

While it had been suggested to add the typically superior image quality and better anatomic context of pre-operatively acquired three-dimensional image data to image data obtained from a two-dimensional projection image, such an approach suffers from the drawback that the relative positions and orientations of the individual vertebrae in the pre-operatively acquired image data may deviate from those in the intra-operative image data (e.g., due to the patient having assumed different positions when the two types of image data were acquired). To avoid the resulting inaccuracy from negatively affecting the navigational information generated by the apparatus 20, each of the pre-operatively acquired image data and the intra-operatively acquired image data may be segmented on a "per-vertebra" basis, followed by determining a transformation per pair of corresponding image segments, that will then be taken into account by the apparatus 20 when generating the surgical information. Such an approach will now be described in more detail with reference to the flow diagram 200 of FIG. 2, the pre-operatively acquired image data (see FIG. 3B and FIGS. 4A to C) and the intra-operatively acquired image data (see FIG. 3A and FIGS. 5A to C).

Figure 2:
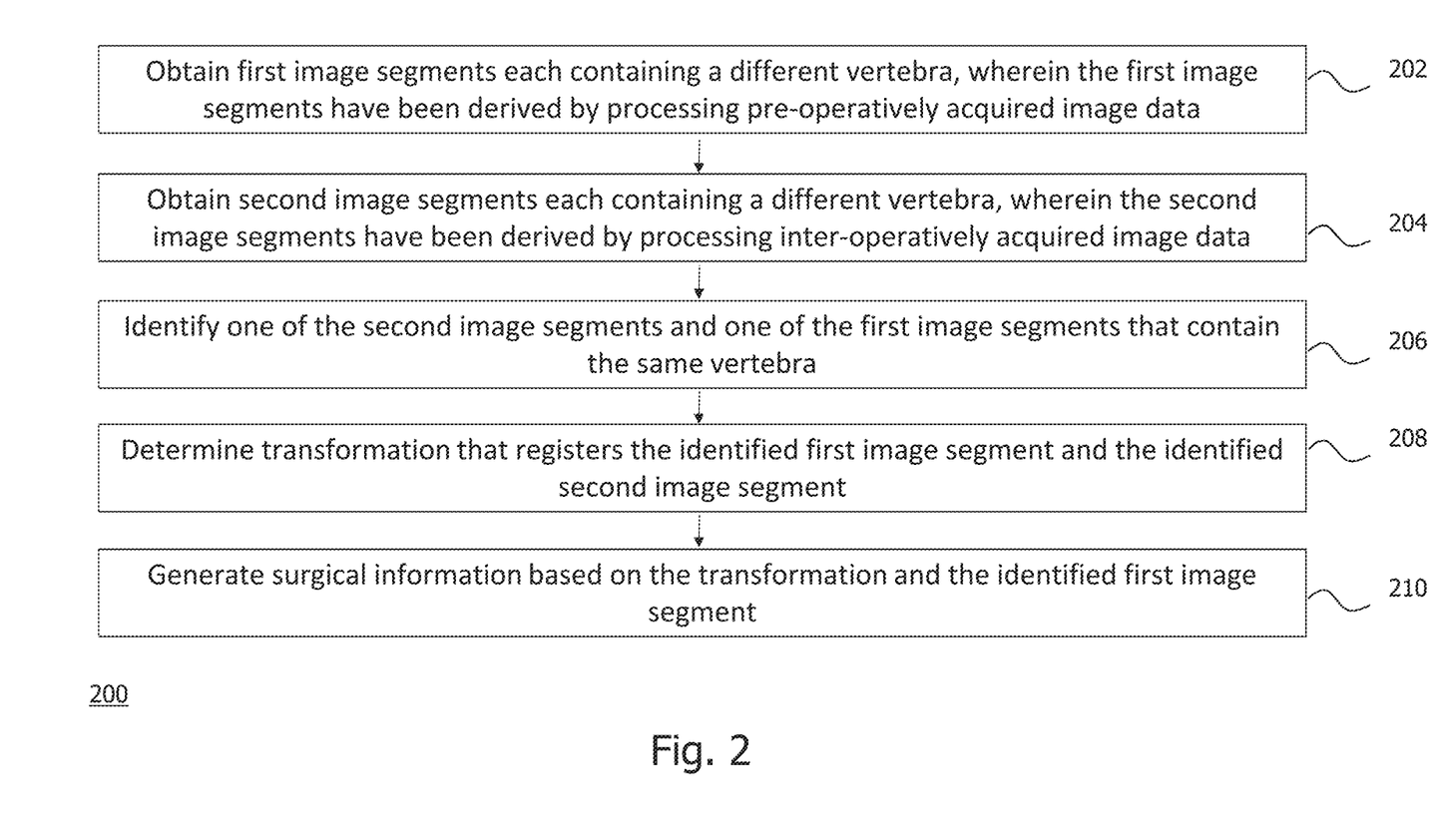
FIG. 2 illustrates a flow diagram of a method implementation of the present disclosure.

The flow diagram 200 of FIG. 2 illustrates a method implementation of the present disclosure as performed by the apparatus 20 in the context of generating surgical information for use by a surgeon or surgical robot. The surgical information is generated from intra-operatively acquired image data of the vertebrae 26 (see FIG. 3A) and from pre-operatively acquired image data of the vertebrae 26 (see FIG. 3B). Exemplary aspects of intra-operative image data acquisition have already been described above with reference to the imaging apparatus 24. Pre-operative image data acquisition may be performed by CT or a magnet resonance imaging (MRI) technique, such as MRT. The corresponding image data may define a three-dimensional image volume (e.g., in the DICOM format).

Figure 3A:
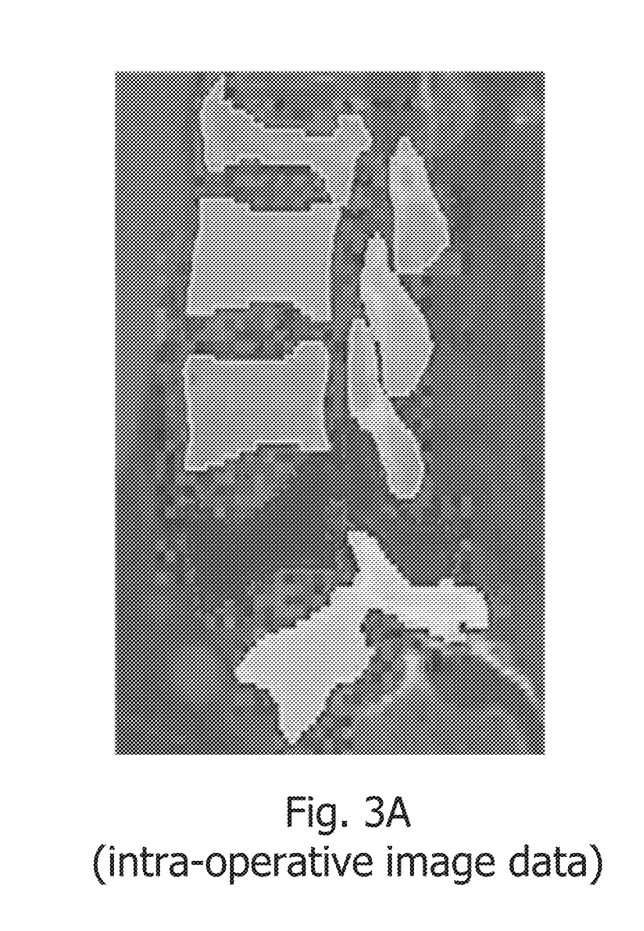
FIG. 3A illustrates a representation of pre-operatively acquired image data of a patient's vertebrae.
Figure 3B:
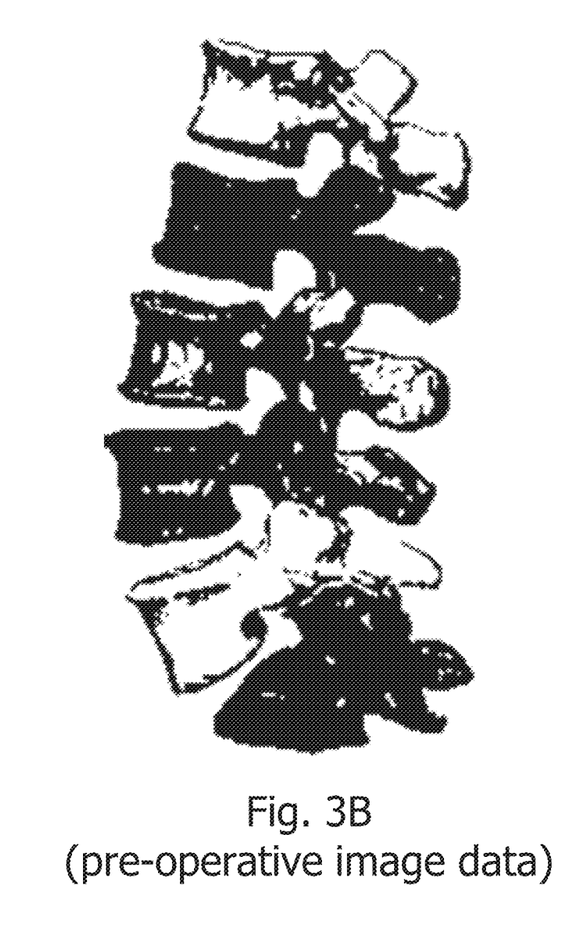
FIG. 3B illustrates a representation of intra-operatively acquired image data of the patient's vertebrae.

In the present scenario, both the pre-operatively acquired image data and the intra-operatively acquired image data contain three-dimensional representations of the vertebrae 26 (although one or both image data could in other scenarios alternatively contain two-dimensional representations). FIGS. 3A and 3B illustrate that the pre-operatively acquired image data have a substantially higher resolution and higher contrast compared to the intra-operatively acquired image data. The intra-operatively acquired image data, on the other hand, still contain valuable information as they are indicative of the current relative positions and relative orientations between the vertebrae 26 during the spinal intervention (i.e., when the patient is positioned on the operating table 34). It has been found that the intra-operative relative positions and the relative orientations of the vertebrae 26 typically differs from those in the pre-operatively acquired image data (e.g., due to different patient positions etc.).

Turning now to step 202 of FIG. 2, the apparatus 20 obtains first image segments 402 each containing a different one of the vertebrae 26. The first image segments 402 are derived (e.g., pre-operatively) by the apparatus 20 or another entity (e.g., a CT imaging apparatus not shown in FIG. 1A) by processing the pre-operatively acquired image data, as illustrated in FIGS. 4A to C.

Figure 4A:
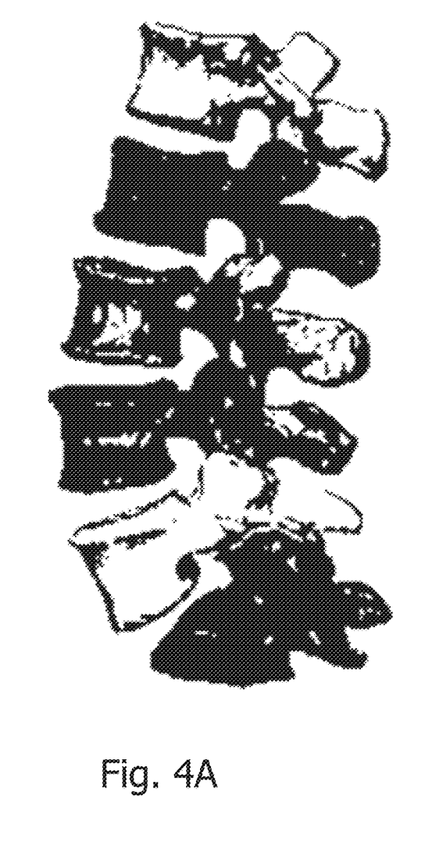
FIGS. 4A-4C schematically illustrate labelling and segmentation of the pre-operatively acquired image data of the patient's vertebrae.
Figure 4B:
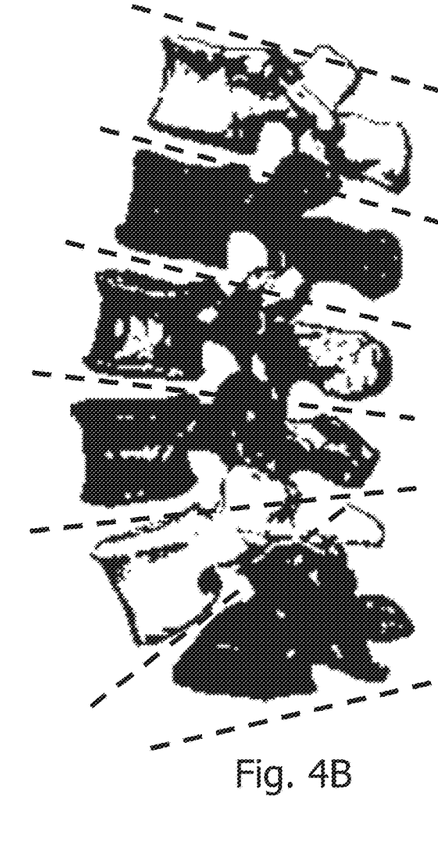

FIG. 4A shows the pre-operatively acquired image data that are initially subjected to a first segmentation step as shown in FIG. 4B. The first segmentation step may be performed in a fully automated manner or based on user input. In the first segmentation step, boundaries (schematically indicated as dashed straight lines in FIG. 4B) are determined between pairs of adjacent vertebrae 26. Since the pre-operatively acquired image data have three spatial dimensions, those boundaries will be two-dimensional geometric entities in the form of, for example, warped planes separating the bony structures of each pair of adjacent vertebrae 26.

Figure 4C:
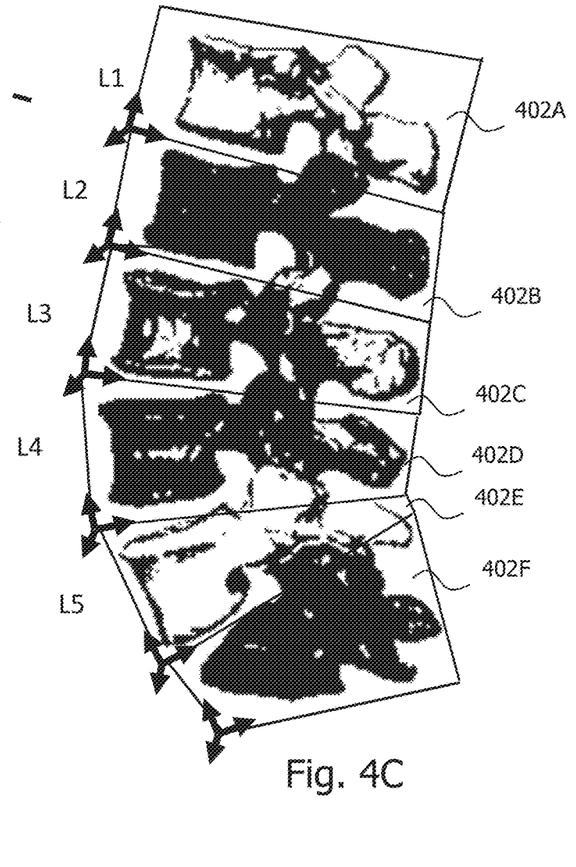

In a second segmentation step illustrated in FIG. 4C, a bounding volume (or "bounding box") is determined in the pre-operatively acquired image data for each of the vertebrae 26. The bounding volume for a given vertebra 26 is limited by the boundaries (see FIG. 4B) towards its adjacent vertebrae 26 and a lateral enclosure extending between those boundaries. The lateral enclosure may be a circumferential structure completely encompassing the vertebra 26 at its sides, while the boundaries limit the lateral enclosure at its top and bottom ends. Like the underlying pre-operatively acquired image data, the bounding volume is a three dimensional structure.

In a third segmentation step, the pre-operatively acquired image data are subjected to a surface identification to identify a vertebra surface (e.g., in the form of a surface mesh) per vertebra 26. Surface identification may be performed using well-known algorithms depending on the format of the image data. If, for example, the image data are indicative of Hounsfield unit (HU) values, threshold-based algorithms may be applied. Alternatively, or additionally, the anatomic context may be taken into account during surface identification (e.g., borders to adjacent vertebrae or other anatomic structures such as the pelvis).

To reduce the computational costs of the surface identification step and to improve segmentation precision, the surface identification is in some variants limited to a the bounding boxes generated in the second segmentation step. As such, the surface identification step is limited to a subset of the pre-operatively acquired image data.

In other variants, the second segmentation step (and, optionally, the first segmentation step) could be skipped and surface segmentation is applied to the pre-operatively acquired image data that have not been (fully) pre-segmented.

The vertebra surface thus determined, such as a data set in three dimensions spanning a surface mesh, in some variants delimits an outer border of an image segment 402 within the pre-operatively acquired image data. In other words, the image segment 402 is defined by the set of pre-operatively acquired image data that fall within the outer border defined by the vertebra surface.

FIG. 4C shows five image segments 402A to 402F, each indicative of the pre-operatively acquired image data associated with a dedicated vertebra 26. As shown in FIG. 4C, each of the image segments 402A to 402F is associated with a dedicated coordinate system rigidly associated therewith (for ease of illustration, the coordinate systems are illustrated at a distance from the image segments 402A to 402F). In some variants, the coordinate systems are anchored at a dedicated surface point (e.g., a vertebral landmark) defined by the surface mesh of each image segment 402A to 402F. Suitable anchor points can be freely selected. As an example, the intervertebral disc adjacent to a given vertebra may be used to define an x-y plane (i.e., the plane in which the x and y axes are located or that extends parallel to the x and y axes) and the z axis may define a depth direction "into" this vertebra. In some variants of this example, or in other examples, a center of mass of a given vertebra (as determined from the respective image data) may be calculated and used as the coordinate system origin for that vertebra.

FIG. 4C also illustrates that vertebral labelling information in the form of an vertebral identifier L1 to L5 is associated with each of the image segments 402A to 402E. This labelling information uniquely denotes each individual one of the vertebrae 26 in accordance with the conventional notation and helps to label and differentiate the individual vertebrae 26 (and image segments 402A to 402E). The labelling information may automatically derived, for example from the vertebra surfaces or other anatomic information in the pre-operatively acquired image data. In some variants, the labelling information is input, or at least validated, by medical personnel (e.g., the surgeon). Such input or validation may be performed in response to the vertebrae 26 being visualized on the output device 22 (e.g., as shown in FIG. 3B).

While not illustrated in the drawings, vertebral landmark identification may be performed for the pre-operatively acquired image data, for example on the basis of the vertebra surfaces. Exemplary landmarks include dedicated points of one or both of the spinous process and the superior articular facet. Landmark detection may be performed automatically or by user input.

Figure 5A:
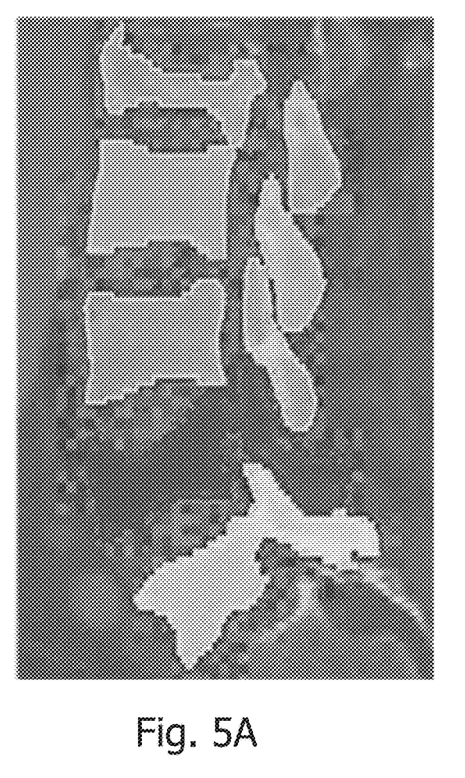
FIGS. 5A-5C schematically illustrate labelling and segmentation of the intra-operatively acquired image data of the patient's vertebrae.
Figure 5B:
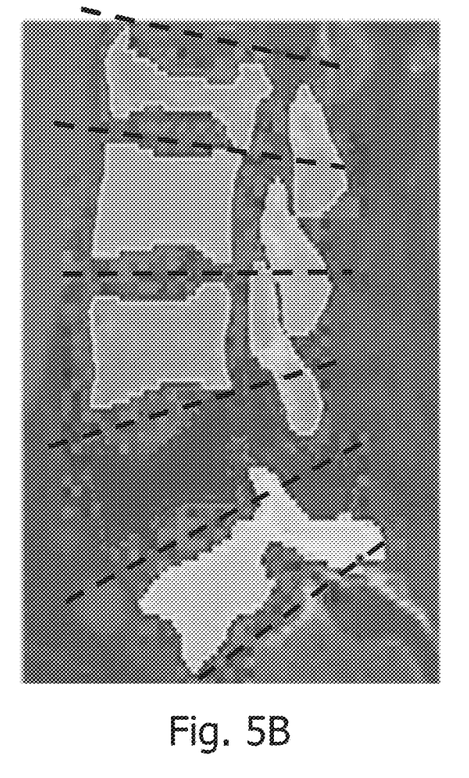
Figure 5C:
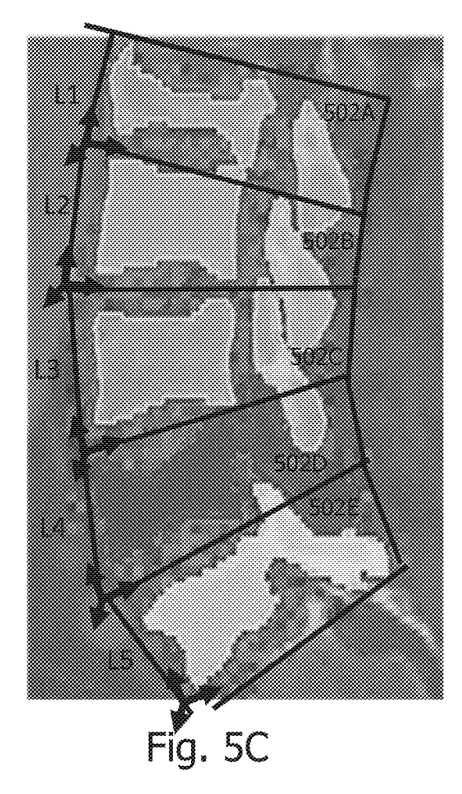

In step 204 of FIG. 2, the apparatus 20 also obtains second image segments 502 each containing a different one of the vertebrae 26. The second image segments are derived intra-operatively by the apparatus 20 or another entity (e.g., the imaging apparatus 24) by processing the intra-operatively acquired image data, as illustrated in FIGS. 5A to C. Since the corresponding processing steps (including surface identification, labelling, landmark identification, etc.) are similar to the ones discussed above with reference to step 202, reference is made to the description above.

It is to be noted that steps 202 and 204 may be performed in any order. Step 202 may be performed intra-operatively or pre-operatively.

In the above variant, it has assumed that the apparatus 20 is configured to process the pre-operatively and intra-operatively acquired image data to obtain the first and segment image segments 402, 502. In other variants, the apparatus 20 is configured to obtain at least one of the first and second image segments 402, 502 via a data carrier, a data link or a data interface. In such variants, the underlying processing of the pre-operatively and intra-operatively acquired image data that yields the first and second image segments 402, 502 has been performed by a different (e.g., a remote) entity.

In step 206, the method continues with identifying individual ones of the second image segments 502 and individual ones of the first image segments 402 that respectively contain the same vertebra 26. This identification step may be performed in various ways, for example based on vertebra surface matching, matching of labelling information or responsive to user input. As an example, the first and second image segments 402, 502 may be identified that are both associated with vertebra 26 of type L1, and similar for other vertebrae 26.

In step 206, each of the first image segments may be compared with each of the second image segments using a surface matching technique. A first and second image segment are determined to contain the same vertebra 26 in case the surface matching is successful for those two image segments (e.g., within a predefined threshold).

The precision of step 206 can be enhanced when using labelling. In a labelling process preceding step 206, each of the first and second image segments may be evaluated with respect to generic vertebra models (that may be pre-defined for different age groups, different sexes, etc. and that may be provided for different vertebra types). The evaluation may be performed using generic vertebra surface information followed by surface matching in regard to each of the first and second image segments. Additionally, or in the alternative, the labelling may be performed based on anatomic context information (e.g., in regard to adjacent anatomic structures such as neighboring vertebrae, the neighboring pelvis, etc.), or otherwise.

In this manner, each of the first and second image segments will first be labelled (e.g., using any type of label, such as L1, L2, etc.), and the resulting labelling information can then be exploited in step 206 to find the first and second image segments with the same label (i.e., that contain the same vertebra 26).

In step 208, at least one transformation is determined that registers the identified first image segment 402 of, for example, vertebra L1 and the identified second image segment of this vertebra L1. It will be appreciated that multiple transformation may be determined for multiple ones of the vertebra (e.g., L1 to L5) based on corresponding ones of the associated first and second image segments 402, 502.

Each of the transformations may be derived by properly matching one or both of the corresponding vertebra surfaces and vertebral landmarks as determined in steps 202 and 204. For example, each transformation may be the result of an optimization algorithm that determines translational and rotational transformation components such that distances between the respective vertebra surfaces and/or vertebral landmarks are minimized. The translational and rotational transformation components may be determined relative to the coordinate systems of each first image segment 402 and the corresponding second image segment 502. For example, each transformation may register the respective coordinate systems.

In some implementations of step 208, the center of gravity is determined first for each image segment. The centers of gravity of the identified first image segment 402 and the corresponding second image segment 502 are matched (e.g., by a translation) in a first step. Then, an alignment of the respective landmarks (e.g., by a rotation and/or a further translation) takes place. Once the landmarks have been properly aligned (e.g., within a predefined threshold), the transformation parameters are known. Instead of (or in addition to, e.g., after) landmark matching, surface matching is performed to determine (or "fine tune") the transformation parameters. Once the surfaces have been properly aligned within a predefined threshold, the transformation parameters are known (or "fined tuned").

In step 210, the surgical information is generated by the apparatus 20 based on the transformation determined in step 208 and based on the first image segment identified in step 206 that is associated with this transformation. There exist various possibilities how the surgical information may be generated in this regard. As an example, the intra-operatively acquired image data can be processed based on one or more of the first image segments 402 and the associated transformation(s). In more detail, one or more of the first image segments 402 derived from the pre-operatively acquired image data of higher image quality are blended into the intra-operatively acquired image data representative of the current position and orientation of the vertebra. The position and orientation at which the one or more first image segments 402 are blended into the intra-operatively acquired image data is defined by the respective transformation(s) as determined in step 208 and, optionally, the region where the corresponding one or more second image segments 502 are located (as defined, e.g., by a center of their coordinate system(s)). Further optionally, a global registration that generally registers the respective intra-operatively and pre-operatively acquired image data may be applied in this context.

Figure 6:
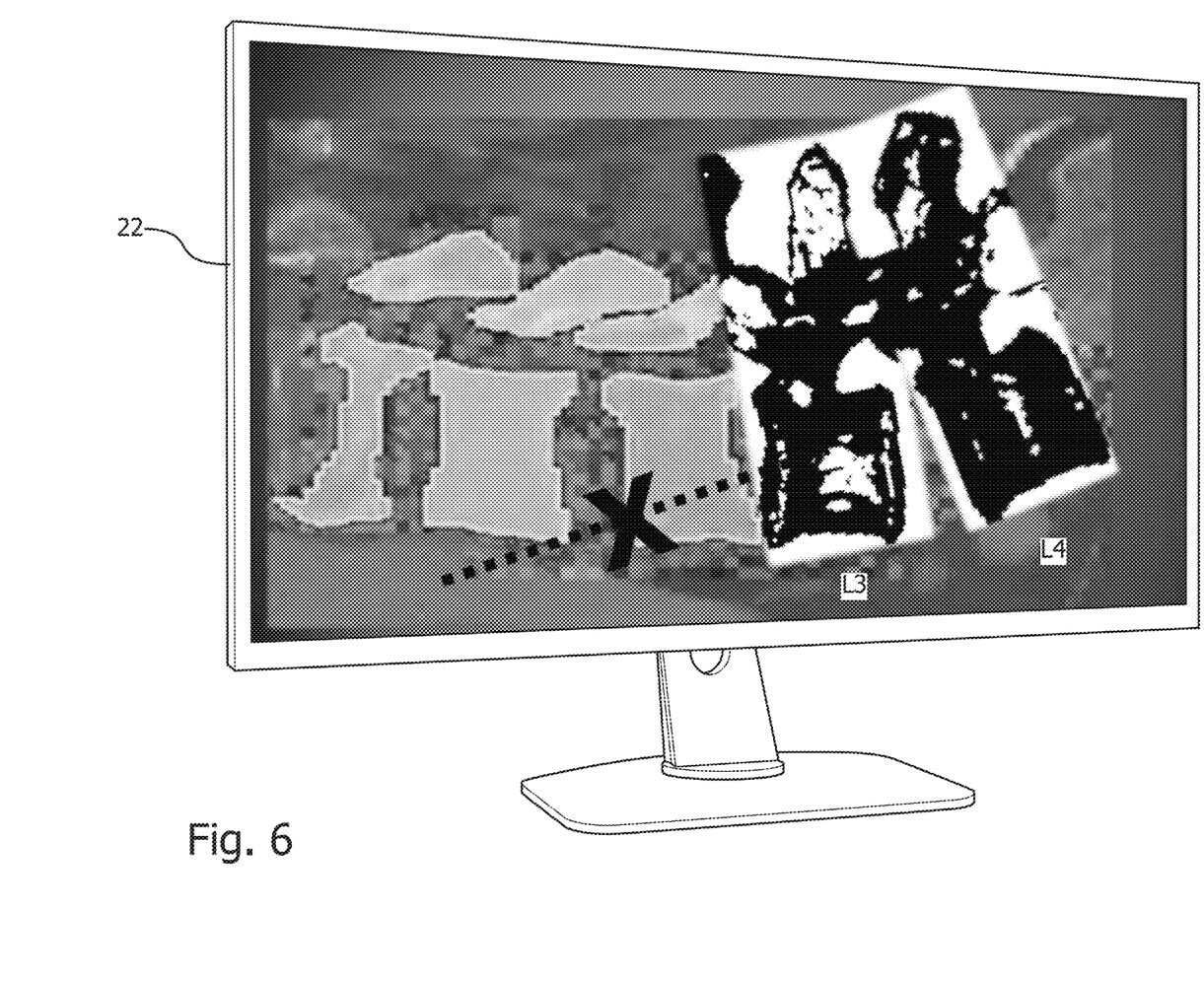
FIG. 6 schematically illustrates the visualization of surgical information generated by the apparatus of FIG. 1A.

The resulting surgical information may be output to a surgeon or surgical robot. FIG. 6 illustrates a scenario in which the surgical information is visually presented to the surgeon on the output device 22 of FIG. 1A. The surgical information comprises a visualization of the intra-operatively acquired image data with enhanced regions at which two first image segments of the pre-operatively acquired image data for vertebrae L3 and L4 are overlaid, or "fused", at their correct anatomical context as defined by the inter-operative position and orientation of the vertebrae L3 and L4 as defined by the intra-operatively acquired image data. As shown in FIG. 6, the labelling information may be visualized also, at least in the context of the first image segments (here: L3 and L4).

The visualization of the surgical information in some variants comprises a plastic three-dimensional representation of the image segments and/or image data (e.g., the vertebrae 26 or parts thereof). Additionally, or as an alternative, the visualization comprises a two-dimensional (e.g., cross-sectional) representation thereof.

The surgical information may continuously be updated in real-time. Updating the surgical information can comprise tracking one or both of the vertebrae L3 and L4 using the tracking system 10 (see FIG. 1A and the exemplary tracker 12 attached to the vertebrae 26) and collectively or individually adapting their visualized position(s) and/or orientation(s) dependent on the tracking. The provision of individual coordinate systems for the vertebrae (see FIGS. 4C and 5C) facilitates the tracking of individual ones of the vertebrae 26 and their corresponding visualization.

Further still, the surgical information may be augmented by tracking the surgical tool 36 (see FIG. 1A) and visualizing on the output device 22 a navigational aid indicative of the tracked surgical tool 36 relative to the visualized vertebrae 26. In the scenario illustrated in FIG. 6, a trajectory and a position of a tool tip are tracked and visualized by a dashed line and a cross, respectively. The surgeon thus obtains visual information on the spatial relationship between the surgical tool 36 and a high-quality representation of the vertebrae L3 and L4.

It is to be noted that instead of using pre-operatively acquired CT image data, also MRI image data may be used in certain variants. MRI image data contains soft tissue information (e.g., about tumors). MRI image data can also be segmented on a "per-vertebra" basis (e.g., to result in surface information) and then be used to enhance the intra-operatively acquired image data.

As has become apparent from the above description of exemplary embodiments, the technique presented herein improves the provision of surgical information and, as such, leads to improved surgical results.

The invention claimed is:

1. A method of generating surgical information from intra-operatively acquired image data of vertebrae and pre-operatively acquired image data of the vertebrae, the method comprising:
    obtaining first image segments each containing a different vertebra, wherein the first image segments have been derived by processing the pre-operatively acquired image data;
    obtaining second image segments each containing a different vertebra, wherein the second image segments have been derived by processing the inter-operatively acquired image data;
    identifying one of the second image segments and one of the first image segments that contain the same vertebra;
    determining a transformation that registers the identified first image segment and the identified second image segment; and
    generating surgical information based on the transformation and the identified first image segment,
    wherein the processing of at least one of the pre-operatively and the intra-operatively acquired image data comprises:
        determining, for an individual vertebra, a bounding volume defining a subset of the respective image data and containing the individual vertebra; and
        performing surface identification to identify a vertebra surface for the individual vertebra in the subset of the respective image data defined by the bounding volume containing the individual vertebra.

2. The method of claim 1, wherein the step of generating the surgical information comprises processing the intra-operatively acquired image data based on the identified first image segment and the transformation.

3. The method of claim 2, wherein the step of processing the intra-operatively acquired image data comprises blending the identified first image segment into the intra-operatively acquired image data with the transformation being applied to the first image segment.

4. The method of claim 1, wherein the steps of identifying, determining, and generating are individually performed for two or more of the first image segments and two or more of the second image segments, respectively.

5. The method of claim 1, wherein the step of processing of at least one of the pre-operatively and the intra-operatively acquired image data comprises determining boundaries in the respective image data between pairs of adjacent vertebrae.

6. The method of claim 5, wherein the bounding volume is limited by the boundaries towards its adjacent vertebrae and a lateral enclosure extending between the two boundaries.

7. The method of claim 1, wherein at least one of the first image segments and the second image segments is defined by, consists of or comprises the vertebra surface of the vertebra contained therein.

8. The method of claim 1, wherein the transformation is determined by matching the vertebra surfaces in the identified second image segment and the identified first image segment.

9. The method of claim 1, further comprising identifying, in at least one of the pre-operatively and the intra-operatively acquired image data, at least one vertebral landmark for an individual vertebra.

10. The method of claim 9, wherein the transformation is determined by matching the vertebral landmarks in the identified second image segment and the identified first image segment.

11. The method of claim 1, wherein the first image segments and the second image segments are each associated with an individual coordinate system, and wherein the transformation registers the coordinate system of the identified second image segment and the coordinate system of the identified first image segment.

12. The method of claim 11, further comprising:
    determining at least one of a rotation and a translation of an individually tracked vertebra during a spinal intervention; and
    taking into account the at least one of the rotation and the translation when generating the surgical information.

13. The method of claim 1, further comprising obtaining labelling information that labels at least some of the first and second image segments, and wherein identifying the first and second image segment that contain the same vertebra is performed based on the labelling information.

14. The method of claim 1, wherein the intra-operatively acquired image data are indicative of at least one of the relative positions and the relative orientations between the vertebrae during a spinal intervention.

15. The method of claim 1, wherein at least one of: (i) at least one of the pre-operatively acquired image data and the intra-operatively acquired image data are representative of a three-dimensional imaging volume, (ii) the pre-operatively acquired image data have a higher resolution than the intra-operatively acquired image data, (iii) at least one of the pre-operatively acquired image data and the intra-operatively acquired image data have been obtained using a radiation-based projection imaging technique.

16. A computer program product stored on memory and comprising program code portions that cause a processor to perform a method when the computer program product is executed by the processor, the method comprising:
   obtaining first image segments each containing a different vertebra, wherein the first image segments have been derived by processing pre-operatively acquired image data;
   obtaining second image segments each containing a different vertebra, wherein the second image segments have been derived by processing inter-operatively acquired image data;
   identifying one of the second image segments and one of the first image segments that contain the same vertebra;
   determining a transformation that registers the identified first image segment and the identified second image segment; and
   generating surgical information based on the transformation and the identified first image segment,
   wherein the processing of at least one of the pre-operatively and the intra-operatively acquired image data comprises:
      determining, for an individual vertebra, a bounding volume defining a subset of the respective image data and containing the individual vertebra; and
      performing surface identification to identify a vertebra surface for the individual vertebra in the subset of the respective image data defined by the bounding volume containing the individual vertebra.

17. An apparatus for generating surgical information from intra-operatively acquired image data of vertebrae and pre-operatively acquired image data of the vertebrae, the apparatus being configured to:
   obtain first image segments each containing a different vertebra, wherein the first image segments have been derived by processing the pre-operatively acquired image data;
   obtain second image segments each containing a different vertebra, wherein the second image segments have been derived by processing the inter-operatively acquired image data;
   identify one of the second image segments and one of the first image segments that contain the same vertebra;
   determine a transformation that registers the identified first image segment and the identified second image segment; and
   generate surgical information based on the transformation and the identified first image segment,
   wherein the processing of at least one of the pre-operatively and the intra-operatively acquired image data comprises:
      determining, for an individual vertebra, a bounding volume defining a subset of the respective image data and containing the individual vertebra; and
      performing surface identification to identify a vertebra surface for the individual vertebra in the subset of the respective image data defined by the bounding volume containing the individual vertebra.

18. The apparatus of claim 17, further configured to update a visual representation of the vertebrae.

* * * * *